United States Patent
Bai et al.

(10) Patent No.: US 10,233,505 B2
(45) Date of Patent: Mar. 19, 2019

(54) CO-DETECTION AND ASSOCIATION OF MULTIPLE GENES FROM THE SAME GENOME IN A SAMPLE

(71) Applicant: Kansas State University Research Foundation, Manhattan, KS (US)

(72) Inventors: Jianfa Bai, Manhattan, KS (US); Xuming Liu, Manhattan, KS (US); Gary Anderson, Manhattan, KS (US)

(73) Assignee: KANSAS STATE UNIVERSITY RESEARCH FOUNDATION, Manhattan, KS (US)

( * ) Notice: Subject to any disclaimer, the term of this patent is extended or adjusted under 35 U.S.C. 154(b) by 0 days.

(21) Appl. No.: 15/543,712

(22) PCT Filed: Jan. 15, 2016

(86) PCT No.: PCT/US2016/013562
§ 371 (c)(1),
(2) Date: Jul. 14, 2017

(87) PCT Pub. No.: WO2016/115441
PCT Pub. Date: Jul. 21, 2016

(65) Prior Publication Data
US 2018/0010170 A1   Jan. 11, 2018

Related U.S. Application Data (60) Provisional application No. 62/104,346, filed on Jan. 16, 2015.

(51) Int. Cl.
*C12Q 1/689* (2018.01)

(52) U.S. Cl.
CPC ....... *C12Q 1/689* (2013.01); *C12Q 2537/143* (2013.01)

(58) Field of Classification Search
None
See application file for complete search history.

(56) References Cited

U.S. PATENT DOCUMENTS

| | | |
|---|---|---|
| 2008/0014578 A1 | 1/2008 | Horikoshi et al. |
| 2008/0176222 A9 | 7/2008 | Hanson et al. |
| 2012/0028342 A1* | 2/2012 | Ismagilov ......... B01L 3/502738 435/283.1 |
| 2013/0122505 A1 | 5/2013 | Tebbs et al. |
| 2013/0224751 A1 | 8/2013 | Olson et al. |
| 2013/0236896 A1 | 9/2013 | Vatta et al. |

FOREIGN PATENT DOCUMENTS

WO   2013186754   12/2013

OTHER PUBLICATIONS

Conrad : Monitoring pathogenic *Escherichia coli* in Alberta Beef Cattle (Masters thesis defended on Dec. 17, 2014 University of Lethbridge, Alberta Canada).*
The International Search Report and Written Opinion dated Apr. 22, 2016, in PCT/US2016/013562, filed Jan. 15, 2016.
Tadmor, Arbel D. "Probing Individual Environmental Bacteria for Viruses by Using Microfluidic Digitak PCR," Science, Jul. 1, 2011, pp. 58-62, vol. 333.
Sharifi Yazdi, MK "Multiplex Polymerase Chain Reaction (PCR) assay for simultaneous detection of shiga-like toxin (stx1 and stx2), intimin (eae) and invasive plasmid antigen H (ipaH) genes in diarrheagenic *Escherichia coli*,"African Journal of Biotechnology, Feb. 28, 2011, pp. 1522-1526, vol. 10(9).
Botkin, Douglas, "Development of a multiplex PCR assay for detection of Shiga toxin-producing *Escherichia coli*, enterohemorrhagic *E. coli*, and enteropathogenic *E. coli* strains," Frontiers in Cellular and Infection Microbiology, Feb. 14, 2012, vol. 2, Article 8.
Bai, J. et al. "Applicability of a multiplex PCR to detect the seven major Shiga toxin-producing *Escherichia coli* based on genes that code for serogroup-specific O-antigens and major virulence factors in cattle feces," Foodborne Pathogens and Disease, Jun. 9, 2012, vol. 9 pp. 541-548.
Bai, J. et al. "A multiplex PCR procedure for the detection of six major virulence genes in *Escherichia coli* O157:H7," J. Microbiological Methods, Jul. 8, 2010, vol. 82, pp. 85-89.
Baker, M. "Digital PCR hits its stride," Nature Methods, 2012, vol. 9, pp. 541-544.
Jacob, M. E. et al. "Evaluation of a multiplex real-time polymerase chain reaction for the quantification of *Escherichia coli* O157 in cattle feces," Foodborne Pathogens and Disease, Jan. 9, 2012, vol. 9, pp. 79-85.
Paddock, Z. et al. Applicability of a multiplex PCR to detect O26, O45, O103, O111, O121, O145, and O157 serogroups of *Escherichia coli* in cattle feces. Vet Microbiology, May 4, 2012, vol. 156, pp. 381-388.
Shen, F. et al.. "Digital PCR on a SlipChip," Lab Chip, Oct. 21, 2010, vol. 10(20) pp. 2666-2672.

* cited by examiner

*Primary Examiner* — Suchira Pande
(74) *Attorney, Agent, or Firm* — Hovey Williams LLP (57) ABSTRACT

The present invention is concerned with PCR-based detection methods and kits for the identification, differentiation, and quantification of different bacterial strains (e.g., Gram-negative bacterial strains), and also association of two or more PCR-positive genes to a single genome. The methods generally comprise carrying out PCR reactions using at least a first PCR primer set and/or probe for at least one target nucleic acid; and a second PCR primer set and/or probe for at least a second target nucleic acid. Positive PCR reaction products are then detected to determine test samples containing positive PCR reaction products for both the first and second target nucleic acids. This information can be used to calculate the gene association rate to determine whether the sample contains, for example, Shiga toxin-producing *E. coli* of the O-type serogroup.

14 Claims, 5 Drawing Sheets
Specification includes a Sequence Listing.

CO-DETECTION AND ASSOCIATION OF MULTIPLE GENES FROM THE SAME GENOME IN A SAMPLE

CROSS-REFERENCE TO RELATED APPLICATIONS

The present application is the National Stage of International Patent Application No. PCT/US2016/013562, filed Jan. 15, 2016, which claims the priority benefit of U.S. Provisional Patent Application Ser. No. 62/104,346, filed Jan. 16, 2015, entitled Co-detection and association of multiple genes from the same *Escherichia coli* genome using digital PCR technology, each of which is incorporated by reference in its entirety herein.

SEQUENCE LISTING

The following application contains a sequence listing in computer readable format (CRF), submitted as a text file in ASCII format entitled "47068-PCTSequenceListing," created on Jan. 14, 2016, as 5 KB. The content of the CRF is hereby incorporated by reference.

BACKGROUND OF THE INVENTION

Field of the Invention

The present invention relates to methods for simultaneous detection (co-detection) of multiple genes, and association of such genes as belonging to the same or multiple genomes, particularly in Gram-negative bacteria.

Description of Related Art

*Escherichia coli* (*E. coli*) are a large and diverse group of Gram-negative bacteria. Although most strains of *E. coli* are harmless, others can lead to severe illness if accidentally ingested. *E. coli* O157:H7 is a kind of *E. coli* that can cause disease by making a toxin called Shiga toxin. Shiga toxin-producing *Escherichia coli* ("STEC") is a major foodborne pathogen that causes more than 175,000 human illnesses and 20-60 deaths in the United States each year. Most deaths and severe illnesses are caused by those that carry virulence genes eae (codes for intimin), stx1 (Shiga toxin 1), and especially stx2 (Shiga toxin 2). Only certain serogroups of STEC, such as O157 and non-O157 serogroups: O26, O45, O103, O111, O121, O145, are of concern for public health. O-groups that carry one or more virulence genes are of particular concern. STECs reside and propagate in the gastrointestinal tract of cattle and shed in the feces, which serve as a major source of food and water contamination. Monitoring and management of STEC in beef production systems has become a very important aspect to public health. USDA Food Safety and Inspection Services (FSIS) requires the industry to test non-intact beef products (mainly ground beef and materials used for ground beef production) to make sure they are free of *E. coli* O157 that carries the eae gene and either one of the stx genes. Regulations for testing six other serogroups (non-O157 STEC) will be in place soon. The current FSIS testing protocols involve a conformational culture isolation procedure that normally takes a week to get a result. The main reason that culture-isolation is required and primarily used is because PCR-based detection methods are not able to associate the virulence genes with the STEC O-groups. Virulence genes can be carried by different bacterial strains in the sample, and normally only *E. coli* O-groups mentioned above that also carry certain virulence genes are considered of concern for public health.

Thus, there remains a significant need in the art to screen food products, and particularly beef and associated processing equipment for target pathogens (e.g., O-type *E. coli*), and likewise determine if the target pathogen carries a virulence gene of concern for public health.

SUMMARY OF THE INVENTION

The present invention is broadly concerned with PCR-based detection methods for the identification, differentiation and quantification of different bacterial strains, and also associate two or more PCR-positive genes to a single genome.

In one aspect, methods for co-detection of two or more target nucleic acid sequences in a sample suspected of or potentially containing Gram-negative bacterial strains (e.g., Shiga toxin-producing *E. coli*), and determination of association of the target nucleic acid sequences as originating from a single genome or from two or more genomes are disclosed. The methods generally comprise providing at least a portion of the sample suspected of or potentially containing the target nucleic acid sequences. A reaction mixture is formed comprising at least a portion of the sample and PCR primers and/or probes corresponding to the two or more target nucleic acid sequences. In one or more embodiments, the PCR primers and/or probes comprise a first PCR primer set and/or probe corresponding to a first target nucleic acid for at least one bacterial serogroup (e.g., *E. coli* O-type); and a second PCR primer set and/or probe corresponding to a second target nucleic acid for at least one bacterial virulence gene. The reaction mixture is divided into a plurality of individual reaction volumes. The reaction volumes are amplified (using PCR) to yield amplified reaction volumes comprising positive PCR reaction products. The number of the amplified reaction volumes containing positive PCR reaction products for both the first and second target nucleic acids (in the same reaction volume). For example, the technique might detect both positive PCR reaction products at least one *E. coli* O-type serogroup and positive PCR reaction products for at least one *E. coli* virulence gene. This information can be used to calculate the gene association rate to determine whether the sample contains toxin-producing bacteria of the concerned serotype.

Also described herein, are kits for co-detection of two or more target nucleic acid sequences in a sample suspected of or potentially containing Gram-negative bacterial strains (e.g., Shiga toxin-producing *E. coli*), and determination of association of the target nucleic acid sequences as originating from a single genome or from two or more genomes. The kits generally comprise instructions for creation of a PCR reaction mixture with the sample, instructions for generation of PCR reaction products from the PCR reaction mixture, and instructions for calculation of a gene association rate based upon the PCR reaction products. The kits can optionally include a variety of components for carrying out the PCR reactions, including one or more of sample collection swabs, containers, buffers, reagents, enzymes, deoxynucleoside triphosphates, primers, and/or probes.

BRIEF DESCRIPTION OF THE DRAWINGS

Figure (FIG. 1A shows an image from digital PCR analysis software for an *E. coli* strain carrying both rfbE and stx2 in a single genome mixed with an *E. coli* strain that does not have the two genes.

DETAILED DESCRIPTION

The present invention is concerned with PCR-based detection methods and kits for the identification, differentiation, and quantification of different bacterial strains (e.g., STEC strains), and also association of two or more PCR-positive genes to a single genome. In the methods, samples are collected from a food product, water, and/or food production system site (e.g., cattle feed yard), food processing equipment (e.g., food contacting surfaces), such as by swabbing, or other conventional techniques. Samples can also be collected from animal waste, food processing by-products, or any other potential contaminated sources in the food production chain. Regardless, the sample will be one suspected of or potentially containing nucleic acid sequences of interest (e.g., such as those associated with STEC strains).

A reaction mixture is then created using at least a portion/aliquot of the sample. Advantageously, the sample does not have to be prepped or purified before use in the inventive methods, and preferably is not subjected to treatment, purification, nucleic acid isolation/extraction, and/or cell lysis procedures before PCR processing. In other words, the sample used to create the reaction mixture preferably remains undisturbed or undisrupted after sample collection, and is not pre-processed, so that potential bacterial contaminants and/or target nucleic acid sequences remain intact in the sample. Accordingly, the sample or portion can be used in the inventive methods directly from its collected state (but may also be diluted or enriched so long as such procedures do not disrupt the potential intact bacterial cells or target nucleic acid in the sample). That is, it will be appreciated most PCR procedures involve initial nucleic acid extraction and/or purification of the sample, which is then used to create the reaction mixture. In this application, no extraction, cell lysis, purification or the like is used on the sample, to ensure adequate presence of target cells or nucleic acids in their intact collected stated.

The reaction mixture is created by mixing the sample, for example, with appropriate buffers, reagents, enzymes (e.g., DNA polymerase), deoxynucleoside triphosphates, primers, probes, and the like for PCR. Exemplary PCR reaction mixture components are commercially-available and include Taqman® Gene Expression Mastermix (Catalog number: 4369016) from Life Technologies/ThermoFisher (Grand Island, N.Y.). In one or more embodiments, the reaction mixture will comprise at least a portion of the sample and a PCR primer set and/or probe. Preferably, the reaction mixture comprises at least a portion of the sample, a PCR primer set (e.g., a first forward primer and a first reverse primer) and a separate probe. The PCR primers and/or probes are designed to amplify and/or detect the target nucleic acids. In one or more embodiments, a first PCR primer set (first forward and reverse primers) and/or first probe is included in the reaction mixture, which corresponds to a target nucleic acid (e.g., gene) for at least one *E. coli* O-type serogroup. In one or more embodiments, a second PCR primer set (second forward and reverse primers) and/or second probe is further included in the reaction mixture, which corresponds to a target nucleic acid for at least one *E. coli* virulence gene. In one or more embodiments, a third PCR primer set (third forward and reverse primers) and/or third probe is included in the reaction mixture, which corresponds to at least a second *E. coli* virulence gene. In one or more embodiments, the virulence genes are selected from the group consisting of stx1, stx2, and eae. In one or more embodiments, a fourth PCR primer set (fourth forward and reverse primers) and/or fourth probe is included in the reaction mixture, which corresponds to a target nucleic acid for at least a second *E. coli* O-type serogroup. In one or more embodiments, a fifth PCR primer set (fifth forward and reverse primers) and/or fifth probe is included in the reaction mixture, which corresponds to a target nucleic acid for at least a third *E. coli* O-type serogroup. Depending upon the multiplexing abilities of the particular PCR instrument, it will be appreciated that additional sixth, seventh, eighth, etc. primer sets and/or probes can be included in the reaction mixture, which correspond to a target nucleic acid for each of the additional *E. coli* O-type serogroups. In one or more embodiments, the reaction mixture can be prepared to detect up to three *E. coli* O-type serotypes and at least two virulence genes (and preferably at least eae, and one of either stx1 or stx2).

Various primer sets or probe designs can be used, depending upon the particular PCR instrument and technique, so long as they correspond to the target nucleic acid. In the case of primers, this generally means that they are complementary to a piece (e.g., 15-25 bp and/or 3' ends) of each of the sense and anti-sense strand of the target nucleic acid. Various primer and probe chemistries can be used. Accordingly, the term "correspond," as used herein means that the primer or probe sequence is designed to be complementary to the target nucleic acid sequence, bind to the target nucleic acid for amplification (e.g., in the case of primers), and/or hybridize with the target nucleic acid (e.g., in the case of probes), but in any event associates in some way with the target nucleic acid in the reaction mixture for amplification and subsequent detection. Exemplary primer sets and probes are listed in the working examples.

In one or more embodiments, the primers and/or probes (and preferably probes) used in the inventive methods include a detectable label, such a dye, fluorophore, or other detectable reporter molecule (and preferably optically detectable reporter molecules). In one or more embodiments, a different reporter molecule is used for each respective target nucleic acid. In one or more embodiments, a first reporter molecule is used for the target nucleic acid for the at least one *E. coli* O-type serogroup. In one or more embodiments, a second reporter molecule is used for the target nucleic acid for the first *E. coli* virulence gene. In one or more embodiments, a third reporter molecule is used for the target nucleic acid for the second *E. coli* virulence gene.

In one or more embodiments, the same reporter molecule is used for each of the virulence genes stx1 and stx2 (and a different reporter molecule is used for virulence gene eae). It will be appreciated that additional (fourth, fifth, sixth, seventh, eighth, etc.) reporter molecules can be used for each of the E. coli O-type serogroups. Specific techniques will depend upon the PCR equipment utilized, including the number of optical channels available in the case of dPCR equipment. Exemplary reporter molecules include FAM (excitation wavelength [EX] 495 nm, emission wavelength [EM] 520 nm), VIC or MAX (EX 538 nm, EM 554 nm), TexasRed (EX 590 nm, EM 610 nm), Cy5 (EX 647 nm, EM 667 nm), and Cy5.5 (EX 690 nm, EM 705 nm).

The reaction mixture is then divided into a plurality of individual reaction volumes for performing PCR reactions. Preferably, the reaction volume is small enough that it can hold only approximately a single nucleic acid molecule (e.g., of a target nucleic acid) or none of the target nucleic acid (if the target nucleic acid is absent from the sample). More particularly, the reaction volume comprises a single nucleic acid molecule, preferably substantially intact, and even more preferably, the volume comprises a single intact bacterial cell containing the target nucleic acid sequence preferably as a substantially intact genome. It will be appreciated that the reaction volume may also comprise none of the nucleic acids or cells in the case of PCR negative reaction volumes. In general, the reaction volume would be less than about 1 nl, and preferably from about 0.5 nl to about 0.9 nl. When the individual reaction volumes are subsequently thermally cycled in a PCR protocol or procedure, the samples containing the target nucleic acid are amplified and produce a positive detection signal, while the samples containing no target nucleic acid are not amplified and produce no detection signal, as applicable. Thus, each positive detection signal is attributable to a single nucleic acid molecule (which may contain one or more of the target nucleic acid sequences).

In one or more embodiments, the reaction mixture is distributed/sub-divided into a plurality of individual reaction wells or chambers (e.g., on a multi-well plate). In one or more embodiments, instead of being distributed into wells, the reaction mixture can be subdivided into individual droplets. The overall approach is same to carrying out the reactions in wells. Thus, PCR is performed to endpoint within each droplet using primers and probes, and a suitable dPCR instrument interrogates each droplet for probe signal, identifying whether the target nucleic acids are present.

Distributing the sample into a plurality of subdivided reaction volumes allows one to estimate the number of different molecules by assuming that the molecule population follows the Poisson distribution. As a result, each reaction volume will theoretically contain zero or one molecule (cell), corresponding to a negative or positive PCR reaction result once PCR end-products are generated via amplification. In conventional PCR, the number of PCR amplification cycles is proportional to the starting copy number. dPCR, however, is not dependent on the number of amplification cycles to determine the initial sample amount, eliminating the reliance on uncertain exponential data to quantify target nucleic acids and therefore can provide accurate quantification.

Regardless, the target nucleic acids in the reaction volumes are amplified according to the selected PCR protocol, followed by detection of the presence of absence of the target nucleic acid in each reaction volume (e.g., well or droplet). In one or more embodiments, amplification involves an initial denaturation at about 95° C. for about 10 minutes followed by about 40 cycles at about 95° C. for about 15 seconds, and about 60° C. for about 60 seconds. As mentioned, the sample in the reaction mixture preferably comprises intact bacteria cells (when present), which in turn contain intact nucleic acids (genomes). The initial denaturation at about 95° C. for about 10 minutes will lyse the cells (if present) and release the target nucleic acids (DNA) for PCR. It will be appreciated that this novel approach not only facilitates determination of whether target nucleic acids originate/reside from the same genome, but also saves time in the overall method, as the samples do not need to be subjected to various pre-processing (e.g., extraction) procedures used in conventional PCR approaches.

In one or more embodiments, signal detection is carried out optically. In one or more embodiments, signal detection is carried out by capturing the signal emitted by each reporter molecule in each cycle of amplification, for example, with a digital camera embedded in the digital PCR system.

The gene association rate is then calculated. The "gene association rate" is calculated by first counting the number of individual reaction volumes that are each positive for at least two of the target nucleic acids, and more preferably are positive for at least one O-serotype and at least one virulence gene. For example, in the case of a two-gene test, one would first count the number of reaction volumes with positive PCR reaction products for both target nucleic acid sequences. Likewise, in the case of a three-gene test, one would first count the number of reaction volumes with positive PCR reaction products for all three target nucleic acid sequences. More particularly, one would count the number of reaction volumes with positive PCR reaction products for at least one O-type serotype nucleic acid sequence and at least one virulence gene nucleic acid sequence (and preferably at least two virulence genes/nucleic acid sequences). In one or more embodiments, a reaction volume would be counted if primer and/or probe signals (as applicable) for at least one O-type serotype nucleic acid sequence is detected in the reaction volume, along with a primer and/or probe signals (as applicable) for a virulence gene nucleic acid sequence for eae, and preferably at least one virulence gene nucleic acid sequence for either of stx1 or stx2. Advantageously, due to the restricted reaction volumes, the presence of two or three signals in the same reaction volume indicates a high likelihood that the target nucleic acid sequences of interest originate from the same genome. Next, the number of reaction volumes that are positive for both: 1) at least one O-serotype nucleic acid sequence, and 2) at least one virulence gene nucleic acid sequence, is divided by the total number of reaction volumes that generate any signal at all (e.g., reaction volumes that have one and two signals for two-gene, and one, two and three signals for three-gene associations). In other words, only reaction volumes with positive PCR end products are counted. Reaction volumes negative for PCR reaction products (i.e., reaction volumes containing no detectable signal) are not counted.

The foregoing calculation yields the gene association rate. When the calculated gene association rate is greater than 50, this indicates that the target nucleic acid sequences originate from the same (a single) genome. As such, the resulting data indicate that the sample contains O-serotype E. coli carrying one or more virulence genes. When the calculated gene association rate is less than 40, this indicates that the target nucleic acid sequences are carried by different genomes. As such, the resulting data may indicate that the sample: 1) does not contain O-serotype E. coli; 2) contains O-serotype E.

*coli* that does not carry virulence genes; and/or 3) contains non-O serotype *E. coli* that carries virulence genes. In any event, such a result indicates that the sample is free of *E. coli* O-serotypes that carry the eae gene and either one of the stx genes, and as such generally confirms the safety of the sample insofar as STEC contamination is concerned. A gene association rate of between 40 and 50 is considered inconclusive and requires further testing and analysis of the sample, including for example, culture isolation of the bacteria.

The current USDA regulation is to test for *E. coli* strains that carry one of the two stx genes and the eae gene. Regulation of testing for the other six O-groups (O26, O45, O103, O111, O121 and O145) that carry the stx and eae genes will be in place soon. The current USDA protocol takes at least a week. The foregoing method, implemented using dPCR yields results in 2 days. Many dPCR machines only have two optical detection channels and a reference channel. In this work, we have been able to adapt the machine to use the reference channel for detection, so that three optical detection channels can be used. USDA guidelines do not dictate which stx gene is present. In certain practically applied embodiments, one could put both stx1 and stx2 in one channel, O-group in a channel, then eae in the 3rd channel. Next generation dPCR machines are advancing towards five channels for detection, which will further expand the possibilities for gene association. Regardless, the present methods permit the association of one of the O-group of *E. coli* carrying stx1/stx2 and eae as being present or absent in the sample. In one or more embodiments, each O-type is tested individually with the virulence genes as a PCR reaction. Accordingly, in some embodiments, seven PCR reactions will be carried out for the seven O-types for each sample. In a given O-type-stx-eae combination, they are labeled with different reporter molecules, but multiple O-types are labeled with the same reporter molecule, and run in different reactions.

This novel method of detection and association of STEC O-type with major virulence genes has broad applications for the beef industry, particularly in regard to meeting current and future USDA food safety regulations. When USDA FSIS requires testing for non-O157 STEC in beef production systems in the near future, this method should have a significant impact and an even larger application for cattle producers, regulatory agencies and consumers.

Major advantages of using digital PCR to detect and to associate STEC O-type with the major virulence genes are to: 1) speed up the entire process from the current one week+ to two days using the inventive approach; and 2) streamline the sample preparation and digital PCR detection processes into a high throughput setting. Co-detection of two or three genes from the same genome out of a diagnostic sample as described here may have broader reaching impact in the field of molecular detection. At a minimum, the inventive co-detection method could be used as a pre-screening method for the existing USDA-FSIS method of Shiga-toxigenic O157 identification. More importantly, it can potentially replace the existing method as well if the method is approved by USDA-FSIS.

Kits for carrying out the various embodiments of the invention are also described herein. Such kits comprise one or more of the following: sample collection swabs, containers (e.g., tubes, vials, flasks), buffers, reagents, enzymes (e.g., DNA polymerase), deoxynucleoside triphosphates, primers, probes, instructions for creation of the PCR reaction mixture, along with instructions for generation of PCR reaction products, and calculation of the gene association rate from the resulting data. The components of the kits will typically be packaged in suitable, respective containers, individually or in pre-mixed forms, and can be provided in aqueous media, in anhydrous buffer, or in lyophilized form.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Pilot Study for dPCR Detection and Association of Multiple Genes

We have developed various PCR-based detection methods for the identification, differentiation and quantification of different STEC strains. A major limitation of these PCR assays is that they are not able to associate two PCR-positive genes to a single genome. For example, a sample testing positive to both rfbE (coding for O157 antigen) and stx2 genes does not necessarily confirm whether the stx2 gene is actually carried by the *E. coli* O157 strain, as other strains in the sample can also carry the stx2 gene. An *E. coli* O157 strain that does not carry stx2 may not be as problematic. The current USDA protocol for identification of STEC O157 stains involves an *E. coli* O157 isolation process through traditional culture method that is tedious, low throughput, and may take up to a week to get the results. We have been investigating the possibility of using digital PCR to associate two or three genes to a single bacterial genome.

Some digital PCR systems distribute a PCR reaction into many tiny reactions to allow absolute quantification of target genes. In this Example, we used the Life Technologies/ Thermo Fisher QuantStudio 3D system (US 2015/0278437, incorporated by reference herein) to perform a pilot study to see if we can co-detect two genes as a proof of concept study. The system is a two-channel (can detect two genes) digital PCR system that aliquots a regular real-time PCR reaction into ~20,000 individual reactions. The system has the largest number of individual reactions for each sample on the market, and thus was selected for initial testing. The size of the reaction well only allows one or a few DNA template molecules to enter, providing the opportunity to associate two genes in a single bacterial cell.

Four E. coli strains were used to generate the preliminary data on the QuantStudio 3D system. Strain 1: an O157 (rfbE) strain that carries stx2 (rfbE+/stx2+); strain 2: a non-O157 strain that does not carry stx2 (rfbE−/stx2−); strain 3: an O157 strain that does not carry stx2 (rfbE+/stx2−); and strain 4: a non-O157 strain that carries stx2 (rfbE−/stx2+). Each of the four E. coli strains stored in −80° C. freezer was streaked on Luria-Bertani (LB) agar plates, and incubated at 37° C. for 16 h to obtain single colonies. A single colony from each strain was inoculated separately into 5 ml LB broth and incubated at 37° C. with shaking for 16 h. The resulting fresh culture is used in the following experiments.

For pure culture testing, 50 µl of overnight culture was inoculated into 5 ml LB broth, and cultured at 37° C. with shaking for 3.5-4 h, until the optical density at 600 nm measured by a spectrophotometer reaches 0.4-0.5 (~$10^8$ CFU/ml). The resulting cultures of strain 1 and strain 2 were mixed in equal volume, and strain 3 and stain 4 were mixed in equal volume. Thus, testing was carried out on an E. coli strain that carries both rfbE and stx2 in a single genome mixed with an E. coli strain that does not have the two genes (mixture of strain 1 and 2), and a mixture of two stains each carry one of the two genes. Each mixture was diluted 150 times with sterile distilled water and used directly as template for digital PCR amplifications.

For cattle fecal spike-in experiment, multiple fecal samples were collected from a cattle feedyard. One gram of each sample was added into 9 ml Escherichia coli (EC) broth, and cultured overnight at 37° C. with shaking, and screened for rfbE and stx2 genes by real-time PCR. A fecal sample that is negative to both rfbE and stx2 was used for culture-inoculation experiment. Fresh cultures (~$10^8$ CFU/ml) of strain 1 and strain 2 were mixed with equal volume; and fresh cultures of strain 3 and strain 4 were mixed with equal volume. Fifty microliter of each culture mixtures was mixed with 0.1 g of feces, respectively, and mixed well. Inoculated feces was added into a 5 ml of EC broth tube, and mixed by low speed vortexing. Five hundred microliter (0.5 ml) of such mixture was inoculated into 4.5 ml EC broth, and incubated at 37° C. for 16 h with shaking. The resulting feces-inoculated culture was diluted to 50 times with sterile distilled water, and used as template for digital PCR.

Figure 1A:
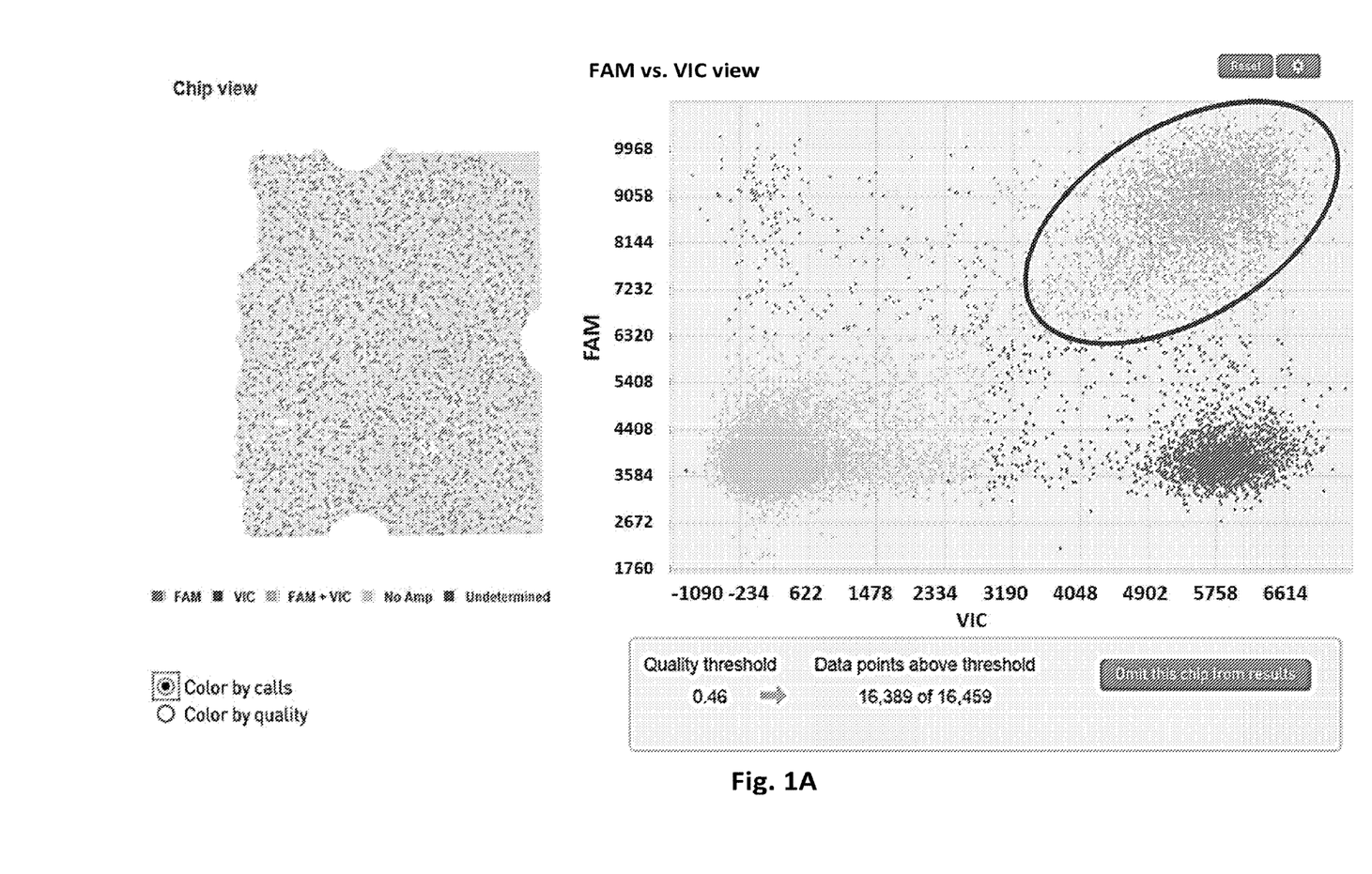
Figure 1B:
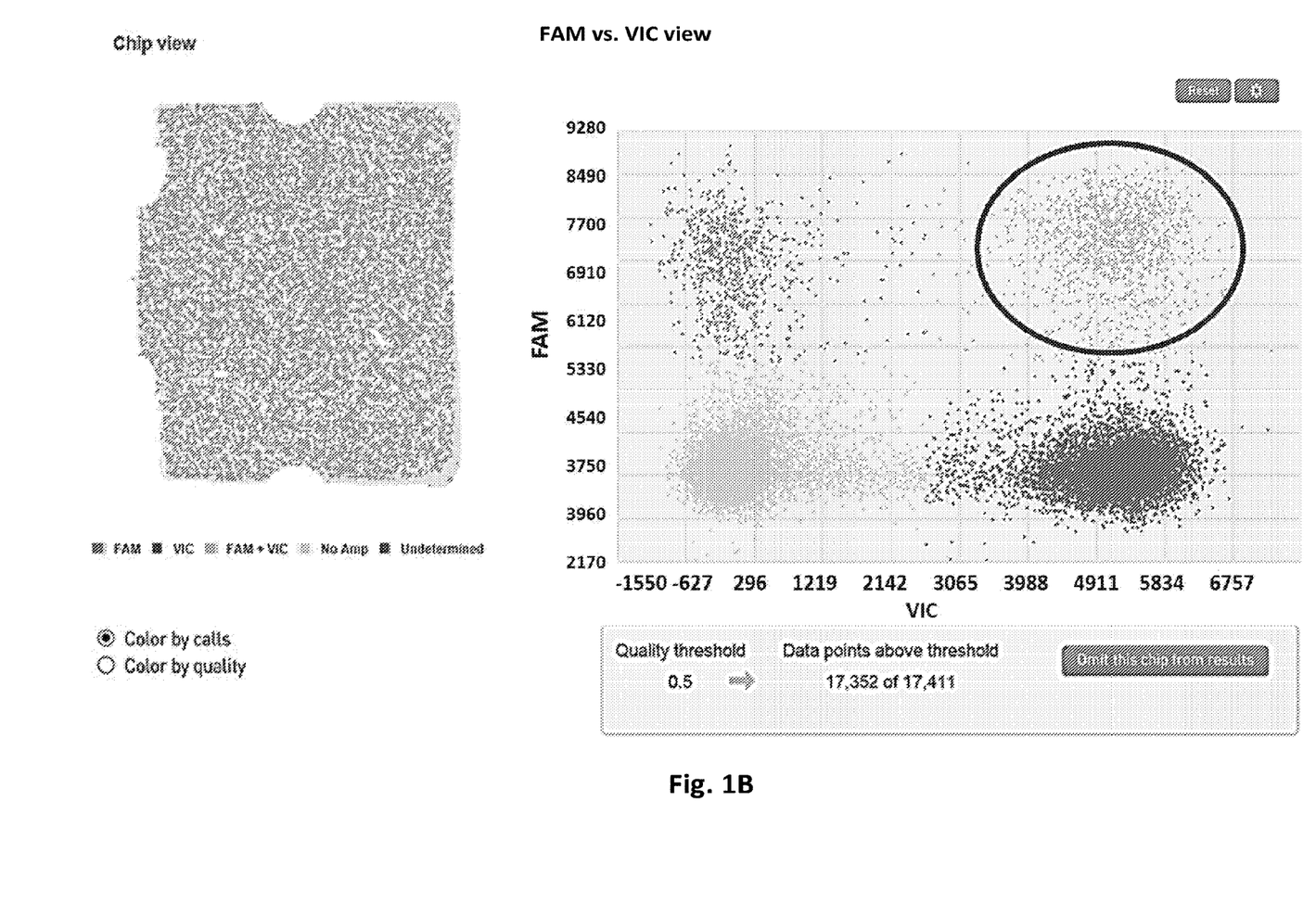
FIG. 1B shows an image from digital PCR analysis software for two *E. coli* stains each carrying only one of the two genes.

Our preliminary data using QuantStudio 3D was able to separate the equal-volume mixture of strains 1 and 2 from the equal-volume mixture of strains 3 and 4. FIGS. 1A and 1B show digital PCR images for the pure E. coli culture results. The results for the mixture of strain 1 and strain 2 are shown in the FIG. 1A, and the results for the mixture of strain 3 and strain 4 are shown in FIG. 1B. The green clusters (encircled portion) are wells that have both genes detected. The number of the green dots in FIG. 1A is greater than that from FIG. 1B indicating that the presence of the two-target genes on a single genome can be differentiated from two genes carried by two different genomes.

Figure 2A:
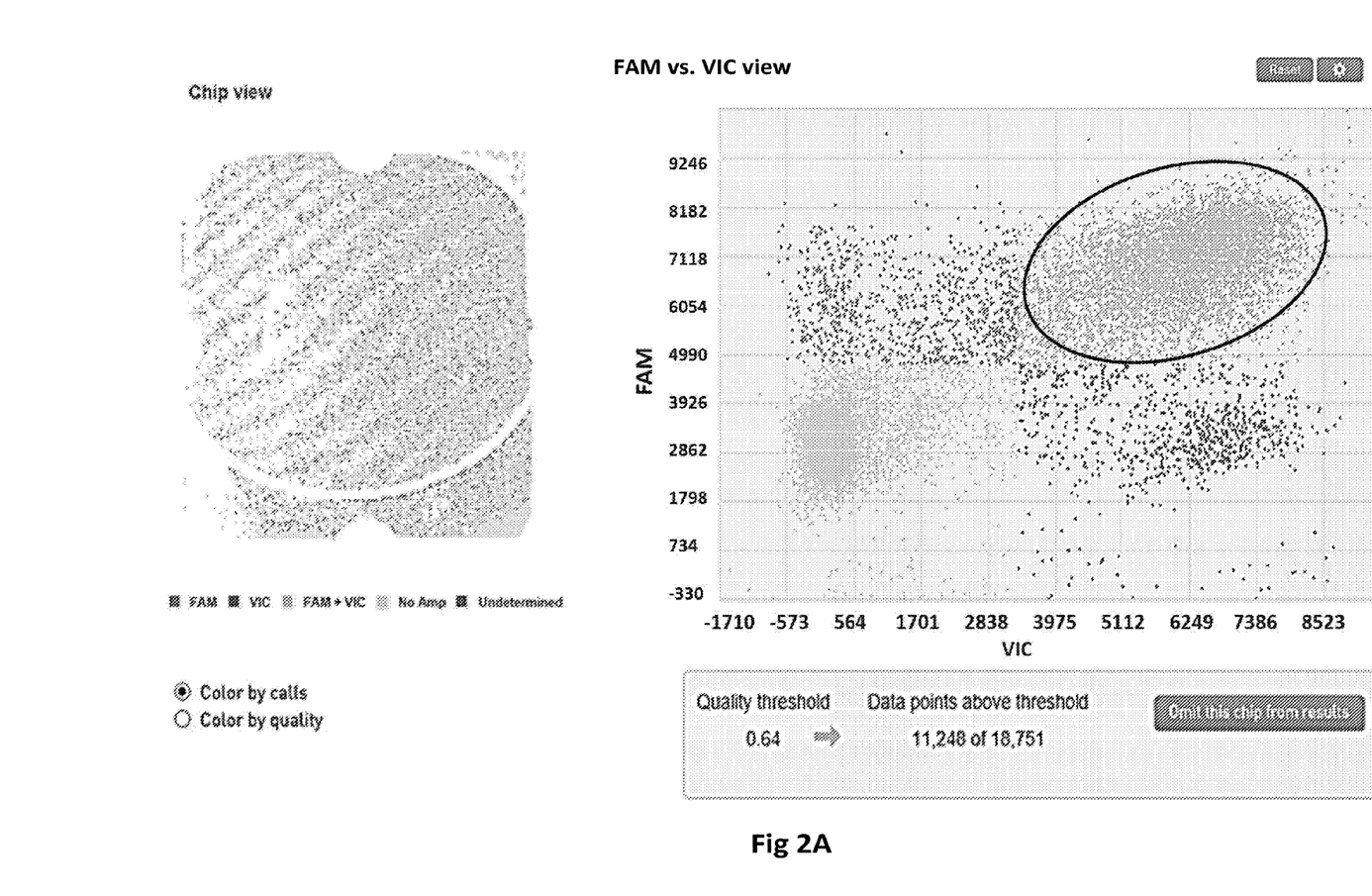
FIG. 2A shows an image from digital PCR analysis software cattle feces spiked with an *E. coli* strain carrying both rfbE and stx2 in a single genome mixed with an *E. coli* strain that does not have the two genes.
Figure 2B:
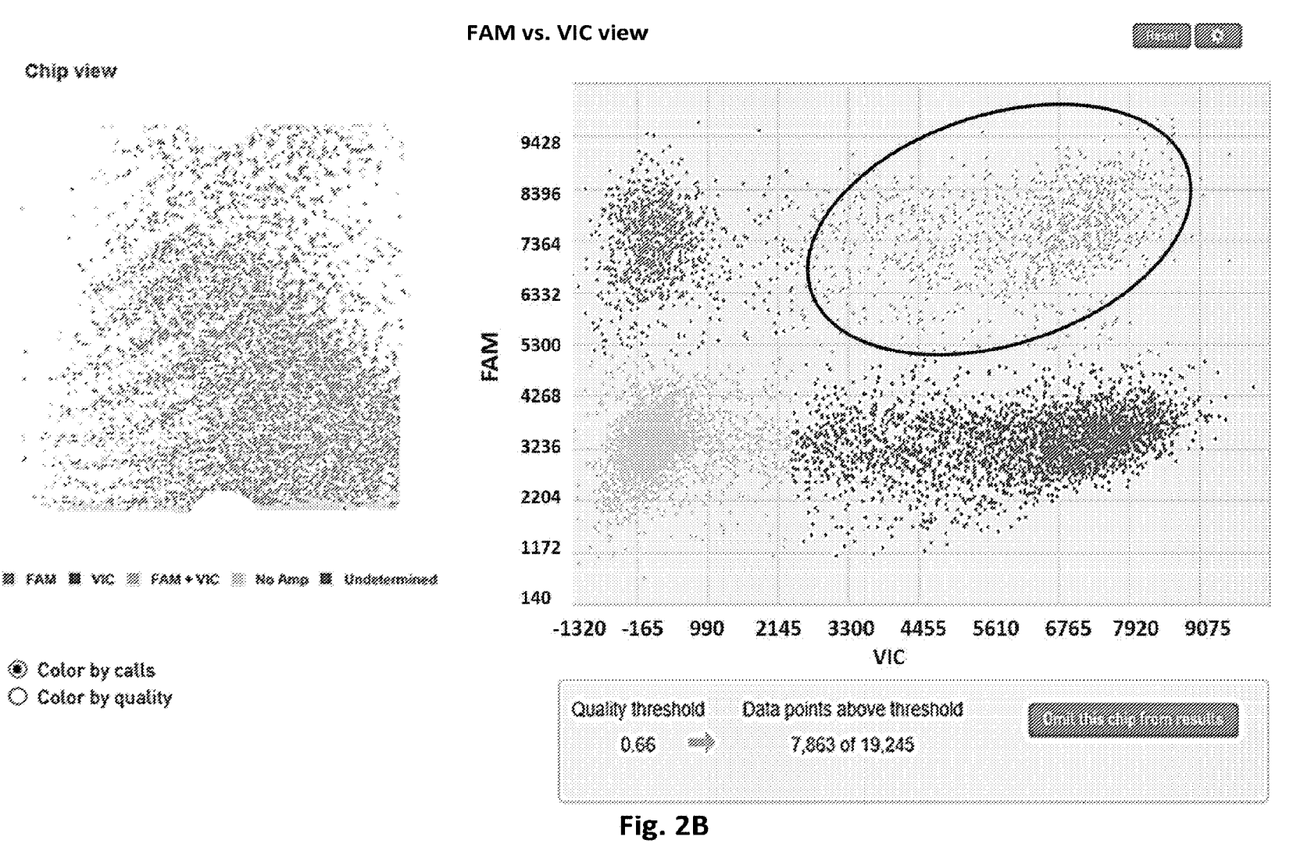
FIG. 2B shows an image from digital PCR analysis software for two *E. coli* stains each carrying only one of the two genes.

FIGS. 2A and 2B show digital PCR images for the cattle feces spiked with pure E. coli culture. The results of the feces spiked with the mixture of strain 1 and strain 2 are shown in FIG. 2A. The results of the feces spiked with the mixture of strain 3 and strain 4 are shown in FIG. 2B. Again, the number of the green dots in FIG. 2A is greater than that from FIG. 2B, indicating that the presence of the two target genes on a single genome can be differentiated from two genes carried by two different genomes in feces samples.

We were able to separate the two mixtures from both pure bacterial cultures (FIGS. 1A&1B) and from cattle fecal samples that were inoculated with the two culture mixtures indicating that the method should work for bovine fecal samples collected in the field (FIGS. 2A & 2B).

Example 2

High Throughput dPCR Detection and Association of Multiple Genes

The protocol used in Example 1 was tested using a high throughput dPCR machine, the Fluidigm Biomark digital PCR platform that can do similar testing but with higher throughput capabilities. The Biomark 48.770 chip is capable of handling 48 samples, each has 770 cells (reactions). Fluidigm kindly provided a demo Biomark machine for this particular study.

We have demonstrated three lines of data with the Biomark system: 1) repeated what we have done with the QuantStudio 3D system which is to associate E. coli O157 antigen with stx2 gene using pure culture and cattle feces inoculated with culture; 2) In addition to serotype O157, we have also tested the six major non-O157 serogroups, namely O26, O45, O103, O111, O121 and O145, and associated them with one of the two stx genes (stx1 or stx2, we do not have an O45 strain that carries stx2 gene in our collection, thus an O45-stx1 strain is used) using pure culture and cattle feces inoculated with culture; and 3) We have tested the association of three genes, O157 antigen, stx2 and eae on the Biomark system. Bacterial culture method and fecal inoculation procedures were the same to that were used for QuantStudio 3D system as described above.

1. Association of O157 Antigen-Encoding Gene rfbE with Stx2 Gene.

Figure 3:
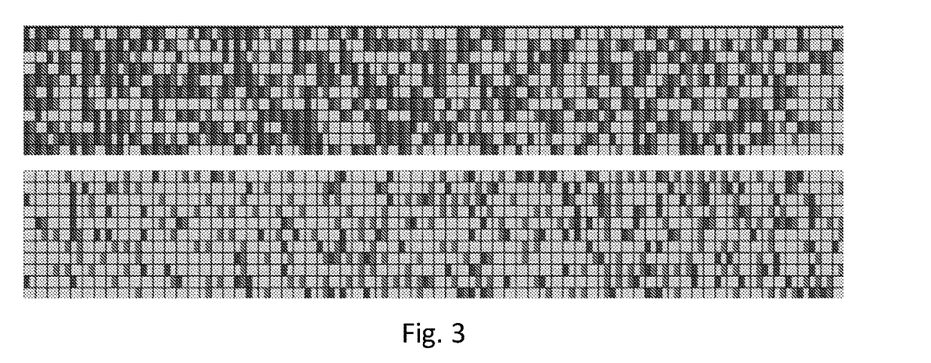
FIG. 3 shows an image from digital PCR analysis software for comparison of rfbE and stx2 genes carried by a single genome (upper panel), versus the same two genes carried by two separate genomes (lower panel)

The same four strains were used: strain 1: an O157 strain that carries stx2 (rfbE+/stx2+); strain 2: a non-O157 strain that does not carry stx2 (rfbE−/stx2−); strain 3: an O157 strain that does not carry stx2 (rfbE+/stx2−); and strain 4: a non-O157 strain that carries stx2 (rfbE−/stx2+). Mixture of strains 1 and 2 (rfbE and stx2 were carried by one strain) was compared with the mixture of strains 3 and 4 (rfbE and stx2 were carried by two separate strains) for both pure culture and for culture-inoculated feces. FIG. 3 shows that the comparison of above-mentioned culture mixtures inoculated into a negative fecal sample. Upper panel is with mixture of strains 1 & 2 (rfbE and stx2 genes carried by a single genome); lower panel is mixture of strains 3 & 4 (rfbE and stx2 genes carried by separate genomes). Number of grids that have two-gene signals (grids have two vertical bars) is significantly higher than those in the lower panel.

TABLE 1

Gene association rate* of top seven E. coli serogroups with Shiga toxin genes analyzed on Biomark system with pure culture and culture inoculated cattle feces.

| E. coli Serogroup and Associated Virulence Genes | Pure Culture | | Culture inoculated feces | |
|---|---|---|---|---|
| | Same Genome | Different Genome | Same Genome | Different Genome |
| O157 and stx2 | 77.6 | 28.7 | 78.6 | 34.5 |
| O26 and stx2 | 56.1 | 14.6 | 57.6 | 14.1 |
| O45 and stx1 | 82.7 | 8.84 | 88.0 | 9.6 |
| O103 and stx2 | 84.5 | 37.3 | 69.3 | 9.8 |
| O111 and stx2 | N/A | N/A | 86.1 | 32.3 |
| O121 and stx2 | N/A | N/A | 83.0 | 38.8 |
| O145 and stx2 | N/A | N/A | 93.3 | 27.7 |
| O157, stx2, and eae | 61.1 | 16.8 | 55.2 | 27.4 |

*Gene association rate was calculated by number of wells that are positive for both genes (two genes tested), or for all three genes (three genes tested), divided by total wells that generate signals (wells that have one and two signals for two-gene, and one, two and three signals for three-gene associations). Pure culture data for O111, O121 and O145 were not generated.

The top row in Table 1 shows the pure culture and culture-inoculated O157 data involving rfbE and stx2 genes. The gene association rate is calculated by number of grids that have two signals, divided by the total number of grids that have one or two signals (percentage of dual positives). The validity of this approach is confirmed by the data. The two genes carried by the same genome had the rate of 77.6 and 78.6 for culture and fecal samples, respectively. Whereas the rate for the two genes carried by separate genomes were 28.7 and 34.5 for culture and fecal samples. These are statistically distinct from the associated rates. This association ratio is significantly higher in mixture of strains 1 & 2, than mixture of strains 3 & 4 for both pure culture and feces inoculated with culture.

2. Association Tests of Non-O157 E. coli Serogroups, O26, O103, O111, O121 and O145 with Stx2, and O45 with Stx1.

Experiment design for the association of non-O157 strains with stx genes is listed in Table 2 below.

TABLE 2

Genotypes and treatments for E. coli non-O157 strain testing

| O-type | Treatment* | Strain genotype | | | | |
|---|---|---|---|---|---|---|
| | | O-group | stx1 | stx2 | Gene tested | |
| O26 | One genome | O26 | + | + | O26 | stx2 |
| | | – | – | – | NA | NA |
| | Two genomes | O26 | + | – | O26 | NA |
| | | – | – | + | NA | stx2 |
| O45 | One genome | O45 | + | – | O45 | stx1 |
| | | – | – | + | NA | NA |
| | Two genomes | O45 | – | – | O45 | NA |
| | | – | + | – | NA | stx1 |
| O103 | One genome | O103 | + | + | O103 | stx2 |
| | | – | – | – | NA | NA |
| | Two genomes | O103 | + | – | O103 | NA |
| | | – | – | + | NA | stx2 |
| O111 | One genome | O111 | + | + | O111 | stx2 |
| | | – | – | – | NA | NA |
| | Two genomes | O111 | + | – | O111 | NA |
| | | – | – | + | NA | stx2 |
| O121 | One genome | O121 | – | + | O121 | stx2 |
| | | – | – | – | NA | NA |
| | Two genomes | O121 | – | – | O121 | NA |
| | | – | + | + | NA | stx2 |
| O145 | One genome | O145 | + | + | O145 | stx2 |
| | | – | – | – | NA | NA |
| | Two genomes | O145 | + | – | O145 | NA |
| | | – | – | + | NA | stx2 |

*"One genome" indicating the two targeted genes are located in a single genome; "Two genomes" indicating the two targeted genes are located on two separate genomes.

Serogroups O26, O45 and O103 were tested with both pure culture and culture-inoculated feces. Serogroups O111, O121 and O145 were tested with culture-inoculated feces. The gene association rates for each serogroup are shown in Table 1. The rates for associated genes in non-O157 strains are between 56.1 and 93.3 with average of 77.8; the rates for unassociated genes are between 9.6 and 38.8 averaged at 21.4. For each pair of comparison, the gene association rates were distinctly different, and easy to differentiate, indicating using this rate we can easily identify those serogroups that carries the virulence genes.

Figure 4:
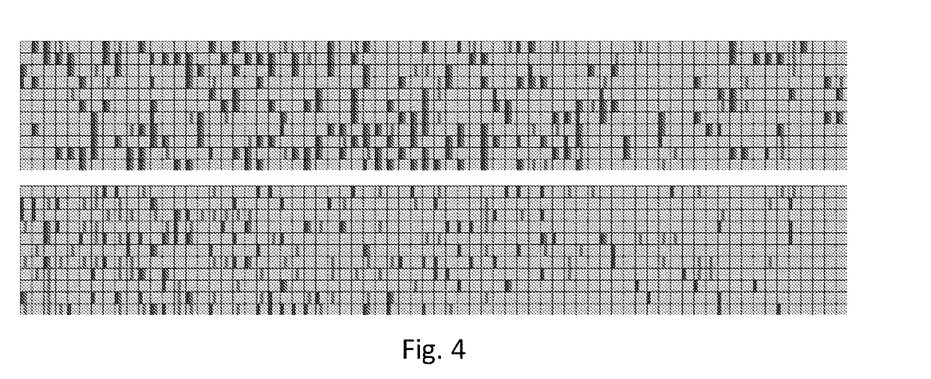
FIG. 4 shows an image from digital PCR analysis software for comparison of O45 and stx1 genes carried by a single genome (upper panel), versus the same two genes carried by two separate genomes (lower panel)

As an example, FIG. 4 shows O45 antigen and stx1 carried by the same genome (upper panel) and these same genes on two separate genomes (lower panel) using culture-inoculated cattle feces. Similar to the O157 data, the number of cells that have two vertical bars in upper panel is obviously larger than the number in the lower panel.

3. Association of O157 Antigen-Encoding Gene (rfbE) with Stx2, and Eae Genes

Figure 5:
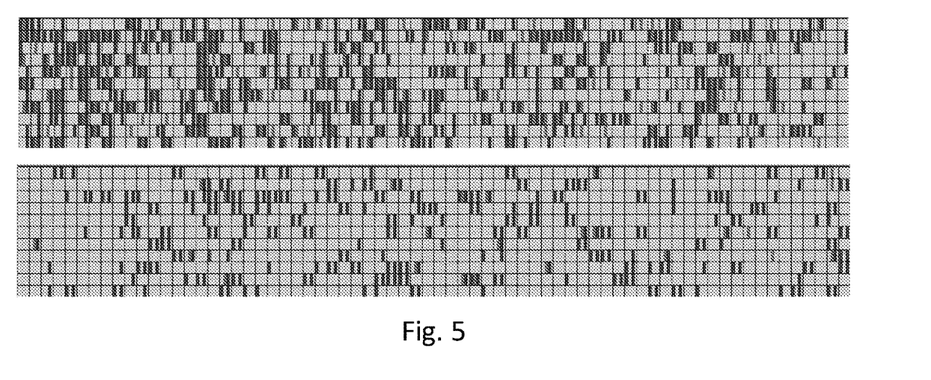
FIG. 5 shows an image from digital PCR analysis software for comparison of rfbE, stx2 and eae genes carried by a single genome (upper panel), versus the same three genes carried by two separate genomes (lower panel).

An E. coli O157 strain (rfbE-positive) that carries both stx2 and eae genes (rfbE+/eae+/stx2+) was mixed with a strain negative to all three genes (rfbE–/eae–/stx2–). This was compared with a mixture of two strains: a) an O157 strain carrying the eae gene (rfbE+/eae+/stx2–); and b) a non-O157 strain carrying only the stx2 gene (rfbE–/eae–/stx2+). Upper panel in FIG. 5 is the strain that carries all three genes; the lower panel is the three genes carried by two separate strains. The number of grids that are positive to all three genes (3 vertical bars in the same cell) in the upper panel is significantly higher than those that in the lower panel. The last row in Table 1 shows that the association rate for three genes carried by a single strain is 61.1 and 55.2 for culture and fecal samples respectively; and the rates for three genes carried by two different strains are 16.8 and 27.4. This data is similar to the two-gene association data we presented for O157 and non-O157 strains above. It will be appreciated that although the data here relates to STEC, this approach will work in other gram-negative bacteria.

TABLE 3

Primers and probes used in digital PCR reactions in this study.

| Target genes/ O-group | Primers/ Probe | Sequence |
|---|---|---|
| wzx$_{O26}$/O26 | Forward | GTGCGAATGCCATATTTCCT (SEQ ID NO: 1) |
| | Reverse | TGCTAGTACTTCACCAACAGCAA (SEQ ID NO: 2) |
| | Probe* | CCTTAGGGGAAAACATCTTTTCAA (SEQ ID NO: 3) |

TABLE 3 -continued

Primers and probes used in digital PCR reactions in this study.

| Target genes/ O-group | Primers/ Probe | Sequence |
|---|---|---|
| $wzx_{O103}$/O103 | Forward | AAAGGCGCATTAGTGTCTGC (SEQ ID NO: 4) |
| | Reverse | GAGGAGTATGTCCCACCCAGT (SEQ ID NO: 5) |
| | Probe | ATGCGGTTGCAGGTGTCTG (SEQ ID NO: 6) |
| $wzx_{O111}$/O111 | Forward | CCGGTTGTTTCATCAATCCT (SEQ ID NO: 7) |
| | Reverse | AAACTAAGTGAGACGCCACCA (SEQ ID NO: 8) |
| | Probe | TGAGTCAAAATGGATGTTTCTTCAA (SEQ ID NO: 9) |
| $wzx_{O45}$/O45 | Forward | GGTGTTGCCATATGGTGTTG (SEQ ID NO: 10) |
| | Reverse | TCCGGAAATTTTACCTTCCA (SEQ ID NO: 11) |
| | Probe | TGATCATGCAACAGGTCACTATGA (SEQ ID NO: 12) |
| $wbqE_{O121}$ + $wbqF_{O121}$/O121 | Forward | TGGATATGCTTCGAATGAACC (SEQ ID NO: 13) |
| | Reverse | CAATGCGAGTTTTGTCTCCA (SEQ ID NO: 14) |
| | Probe | TTCCTACACCTACTCGATATACTCCCA (SEQ ID NO: 15) |
| $WZX_{O145}$/O145 | Forward | CATTGTTTTGCTTGCTCGAC (SEQ ID NO: 16) |
| | Reverse | CAACGAAAATACCATATCCTACAGC (SEQ ID NO: 17) |
| | Probe | CCATCAACAGATTTAGGAGTGTATGG (SEQ ID NO: 18) |
| $rfbE_{O157}$/O157 | Forward | TAGGACCGCAGAGGAAAGAG (SEQ ID NO: 19) |
| | Reverse | AAACTGGCCTTGTTTCGATG (SEQ ID NO: 20) |
| | Probe | TCTGCAAGGTGATTCCTTAATTCCT (SEQ ID NO: 21) |
| stx1 | Forward | CAAGAGCGATGTTACGGTTTG (SEQ ID NO: 22) |
| | Reverse | GTAAGATCAACATCTTCAGCAGTC (SEQ ID NO: 23) |
| | Probe | ACATAAGAACGCCCACTGAGATCATCCA (SEQ ID NO: 24) |
| stx2 | Forward | GCATCCAGAGCAGTTCTGC (SEQ ID NO: 25) |
| | Reverse | GCGTCATCGTATACACAGGAG (SEQ ID NO: 26) |
| | Probe | TGTCACTGTCACAGCAGAAGCCTTACG (SEQ ID NO: 27) |
| eae | Forward | AAAGCGGGAGTCAATGTAACG (SEQ ID NO: 28) |
| | Reverse | GGCGATTACGCGAAAGATAC (SEQ ID NO: 29) |
| | Probe | CTCTGCAGATTAACCTCTGCCG (SEQ ID NO: 30) |

*All probes for the O-group and stx gene pair were labeled with FAM and MAX (VIC equivalent; i.e., FAM for O157 and MAX for stx2; MAX for O103 and FAM for stx2, etc.), except that the eae gene on the third channel was labeled with TexasRed. All quenchers were used as manufacturer suggested.

We claim:

1. A method for co-detection of two or more target nucleic acid sequences in a sample suspected of or potentially containing Gram-negative bacteria, and determination of association of said target nucleic acid sequences as originating from a single genome or from two or more genomes, said method comprising:
   providing a sample suspected of or potentially containing said target nucleic acid sequences;
   forming a reaction mixture comprising at least a portion of said sample and PCR primers and/or probes corresponding to said two or more target nucleic acid sequences, wherein said sample may be diluted or enriched, but is not subjected to nucleic acid isolation, extraction, purification, or cell lysis, before forming said reaction mixture, said PCR primers and/or probes comprising:
      a first PCR primer set and/or probe corresponding to a first target nucleic acid for at least one Gram-negative bacterial serogroup or genotype; and
      a second PCR primer set and/or probe corresponding to a second target nucleic acid for at least one virulence gene from a Gram-negative bacteria;
   dividing said reaction mixture into a plurality of individual reaction volumes of less than about 1 nl, wherein said reaction volume comprises up to a single intact bacterial cell or single intact nucleic acid molecule;
   amplifying said reaction volumes to yield amplified reaction volumes comprising positive PCR reaction products;
   detecting the total number of amplified reaction volumes containing at least one positive PCR reaction product and the number of said amplified reaction volumes containing both positive PCR reaction products for said first target nucleic acid and positive PCR reaction products for said second target nucleic acid; and
   calculating a gene association rate for said amplified reaction volumes by dividing the number of amplified reaction volumes containing both positive PCR reaction products by the total number of amplified reaction volumes containing at least one positive reaction product to yield said gene association rate, wherein if the gene association rate is greater than 50%, then the two or more target nucleic acid sequences originate from the same genome, and if the gene association rate is less than 40% then the two or more target nucleic acid sequences originate from different genomes.

2. The method of claim 1, wherein said reaction mixture further comprise one or more buffers, reagents, enzymes, and/or deoxynucleoside triphosphates.

3. The method of claim 1, wherein said first and/or second primer set and/or probe comprises a detectable reporter molecule.

4. The method of claim 1, wherein said dividing comprises distributing said reaction mixture into a plurality of individual reaction wells or chambers, each well or chamber comprising respective reaction volumes.

5. The method of claim 1, wherein said dividing comprises generation of a plurality of individual droplets of said reaction mixture, each droplet comprising respective reaction volumes.

6. The method of claim 1, wherein said Gram-negative bacteria is Shiga toxin-producing *Escherichia coli*.

7. The method of claim 1, wherein said first PCR primer set and/or probe corresponds to a target nucleic acid for at least one *E. coli* 0-type serogroup; and said second PCR primer set and/or probe corresponds to a target nucleic acid for at least one *E. coli* virulence gene.

8. The method of claim 7, wherein said virulence gene is selected from the group consisting of stx1, stx2, and eae.

9. The method of claim 7, wherein said positive PCR reaction products for at least one *E. coli* 0-type serogroup is a detectable signal from a primer/probe for said 0-type serotype and said and positive PCR reaction products for at least one *E. coli* virulence gene is a detectable signal from a primer/probe for virulence gene eae, stx1, or stx2.

10. The method of claim 7, wherein said *E. coli* O-type serogroup is selected from the group consisting of O157, O26, O45, O103, O111, O121, and O145.

11. The method of claim 7, wherein said reaction mixture further comprises a third PCR primer set and/or probe corresponding to at least a second *E. coli* virulence gene.

12. The method of claim 7, wherein said reaction mixture further comprises a fourth PCR primer set and/or probe corresponding to a target nucleic acid for at least a second *E. coli* 0-type serogroup.

13. The method of claim 7, wherein said first PCR primer set and/or probe corresponding to a target nucleic acid for at least one *E. coli* 0-type serogroup is selected from the group consisting of SEQ ID NOs: 1, 2, 3, 4, 5, 6, 7, 8, 9, 10, 11, 12, 13, 14, 15, 16, 17, 18, 19, 20, 21, and combinations thereof.

14. The method of claim 7, wherein said second PCR primer set and/or probe corresponding to a target nucleic acid for at least one *E. coli* virulence gene is selected from the group consisting of SEQ ID NOs: 22, 23, 24, 25, 26, 27, 28, 29, 30, and combinations thereof.

\* \* \* \* \*

SEQUENCE LISTING

<160> NUMBER OF SEQ ID NOS: 30

<210> SEQ ID NO 1
<211> LENGTH: 20
<212> TYPE: DNA
<213> ORGANISM: Escherichia coli

<400> SEQUENCE: 1
gtgcgaatgc catatttcct                                              20

<210> SEQ ID NO 2
<211> LENGTH: 23
<212> TYPE: DNA
<213> ORGANISM: Escherichia coli

<400> SEQUENCE: 2
tgctagtact tcaccaacag caa                                          23

<210> SEQ ID NO 3
<211> LENGTH: 24
<212> TYPE: DNA
<213> ORGANISM: Escherichia coli

<400> SEQUENCE: 3

```
ccttagggga aaacatcttt tcaa                                        24

<210> SEQ ID NO 4
<211> LENGTH: 20
<212> TYPE: DNA
<213> ORGANISM: Escherichia coli

<400> SEQUENCE: 4
aaaggcgcat tagtgtctgc                                             20

<210> SEQ ID NO 5
<211> LENGTH: 21
<212> TYPE: DNA
<213> ORGANISM: Escherichia coli

<400> SEQUENCE: 5
gaggagtatg tcccacccag t                                           21

<210> SEQ ID NO 6
<211> LENGTH: 19
<212> TYPE: DNA
<213> ORGANISM: Escherichia coli

<400> SEQUENCE: 6
atgcggttgc aggtgtctg                                              19

<210> SEQ ID NO 7
<211> LENGTH: 20
<212> TYPE: DNA
<213> ORGANISM: Escherichia coli

<400> SEQUENCE: 7
ccggttgttt catcaatcct                                             20

<210> SEQ ID NO 8
<211> LENGTH: 21
<212> TYPE: DNA
<213> ORGANISM: Escherichia coli

<400> SEQUENCE: 8
aaactaagtg agacgccacc a                                           21

<210> SEQ ID NO 9
<211> LENGTH: 25
<212> TYPE: DNA
<213> ORGANISM: Escherichia coli

<400> SEQUENCE: 9
tgagtcaaaa tggatgtttc ttcaa                                       25

<210> SEQ ID NO 10
<211> LENGTH: 20
<212> TYPE: DNA
<213> ORGANISM: Escherichia coli

<400> SEQUENCE: 10
ggtgttgcca tatggtgttg                                             20

<210> SEQ ID NO 11
<211> LENGTH: 20
<212> TYPE: DNA
<213> ORGANISM: Escherichia coli
```

<400> SEQUENCE: 11 tccgaaatt ttaccttcca                                        20

<210> SEQ ID NO 12
<211> LENGTH: 24
<212> TYPE: DNA
<213> ORGANISM: Escherichia coli

<400> SEQUENCE: 12
tgatcatgca acaggtcact atga                                  24

<210> SEQ ID NO 13
<211> LENGTH: 21
<212> TYPE: DNA
<213> ORGANISM: Escherichia coli

<400> SEQUENCE: 13
tggatatgct tcgaatgaac c                                     21

<210> SEQ ID NO 14
<211> LENGTH: 20
<212> TYPE: DNA
<213> ORGANISM: Escherichia coli

<400> SEQUENCE: 14
caatgcgagt tttgtctcca                                       20

<210> SEQ ID NO 15
<211> LENGTH: 27
<212> TYPE: DNA
<213> ORGANISM: Escherichia coli

<400> SEQUENCE: 15
ttcctacacc tactcgatat actccca                               27

<210> SEQ ID NO 16
<211> LENGTH: 20
<212> TYPE: DNA
<213> ORGANISM: Escherichia coli

<400> SEQUENCE: 16
cattgttttg cttgctcgac                                       20

<210> SEQ ID NO 17
<211> LENGTH: 25
<212> TYPE: DNA
<213> ORGANISM: Escherichia coli

<400> SEQUENCE: 17
caacgaaaat accatatcct acagc                                 25

<210> SEQ ID NO 18
<211> LENGTH: 26
<212> TYPE: DNA
<213> ORGANISM: Escherichia coli

<400> SEQUENCE: 18
ccatcaacag atttaggagt gtatgg                                26

<210> SEQ ID NO 19
<211> LENGTH: 20
<212> TYPE: DNA
<213> ORGANISM: Escherichia coli -continued

<400> SEQUENCE: 19
taggaccgca gaggaaagag                                              20

<210> SEQ ID NO 20
<211> LENGTH: 20
<212> TYPE: DNA
<213> ORGANISM: Escherichia coli

<400> SEQUENCE: 20
aaactggcct tgtttcgatg                                              20

<210> SEQ ID NO 21
<211> LENGTH: 25
<212> TYPE: DNA
<213> ORGANISM: Escherichia coli

<400> SEQUENCE: 21
tctgcaaggt gattccttaa ttcct                                        25

<210> SEQ ID NO 22
<211> LENGTH: 21
<212> TYPE: DNA
<213> ORGANISM: Escherichia coli

<400> SEQUENCE: 22
caagagcgat gttacggttt g                                            21

<210> SEQ ID NO 23
<211> LENGTH: 24
<212> TYPE: DNA
<213> ORGANISM: Escherichia coli

<400> SEQUENCE: 23
gtaagatcaa catcttcagc agtc                                         24

<210> SEQ ID NO 24
<211> LENGTH: 28
<212> TYPE: DNA
<213> ORGANISM: Escherichia coli

<400> SEQUENCE: 24
acataagaac gcccactgag atcatcca                                     28

<210> SEQ ID NO 25
<211> LENGTH: 19
<212> TYPE: DNA
<213> ORGANISM: Escherichia coli

<400> SEQUENCE: 25
gcatccagag cagttctgc                                               19

<210> SEQ ID NO 26
<211> LENGTH: 21
<212> TYPE: DNA
<213> ORGANISM: Escherichia coli

<400> SEQUENCE: 26
gcgtcatcgt atacacagga g                                            21

<210> SEQ ID NO 27
<211> LENGTH: 27
<212> TYPE: DNA

```
<213> ORGANISM: Escherichia coli

<400> SEQUENCE: 27
tgtcactgtc acagcagaag ccttacg                                          27

<210> SEQ ID NO 28
<211> LENGTH: 21
<212> TYPE: DNA
<213> ORGANISM: Escherichia coli

<400> SEQUENCE: 28
aaagcgggag tcaatgtaac g                                                21

<210> SEQ ID NO 29
<211> LENGTH: 20
<212> TYPE: DNA
<213> ORGANISM: Escherichia coli

<400> SEQUENCE: 29
ggcgattacg cgaaagatac                                                  20

<210> SEQ ID NO 30
<211> LENGTH: 22
<212> TYPE: DNA
<213> ORGANISM: Escherichia coli

<400> SEQUENCE: 30
ctctgcagat taacctctgc cg                                               22
```